US006177577B1

(12) United States Patent
Roerden et al.

(10) Patent No.: US 6,177,577 B1
(45) Date of Patent: Jan. 23, 2001

(54) DICATIONIC AND POLYCATIONIC MONOPRIMARY ALCOHOLS AND DERIVATIVES THEREOF

(75) Inventors: Dorothy L. Roerden; R. Keith Frank, both of Lake Jackson, TX (US)

(73) Assignee: The Dow Chemical Company, Midland, MI (US)

(*) Notice: Under 35 U.S.C. 154(b), the term of this patent shall be extended for 0 days.

(21) Appl. No.: 07/792,553

(22) Filed: Nov. 15, 1991

(51) Int. Cl.[7] .................. C07D 303/36; C07C 211/63
(52) U.S. Cl. .................. 549/551; 549/555; 549/558; 549/563; 564/295
(58) Field of Search ................. 549/551, 555, 549/558, 563; 564/295

(56) References Cited

U.S. PATENT DOCUMENTS

| | | | |
|---|---|---|---|
| 3,532,751 | 10/1970 | Langher et al. | 260/567.6 |
| 3,567,729 | 3/1971 | Lewis et al. | 260/268 |
| 3,632,559 | 1/1972 | Matter et al. | 260/78 |
| 3,755,160 | 8/1973 | Witt | 210/54 |
| 4,054,542 | 10/1977 | Buckman et al. | 260/2 BP |
| 4,093,605 | 6/1978 | Hoppe et al. | 260/78 SC |
| 4,127,563 | 11/1978 | Rankin et al. | 536/50 |
| 4,156,775 | 5/1979 | Evani et al. | 528/421 |
| 4,281,109 | 7/1981 | Jarowenko et al. | 536/50 |
| 4,332,935 | 6/1982 | Fischer et al. | 536/50 |
| 4,385,184 * | 5/1983 | Hamanaka et al. | 549/551 |
| 4,464,528 | 8/1984 | Tasset | 536/50 |
| 4,602,110 | 7/1986 | Tasset | 564/292 |
| 4,737,576 | 4/1988 | Bachem et al. | 528/405 |
| 4,812,263 * | 3/1989 | Login | 564/295 |
| 4,992,536 | 2/1991 | Billmers et al. | 536/55.1 |

FOREIGN PATENT DOCUMENTS 406837   1/1991   (EP) .

OTHER PUBLICATIONS

Wurzburg, ed., "Modified Starches: Properties and Uses" CRC Press, Inc. (1986) p. 122.

* cited by examiner

Primary Examiner—Ba K. Trinh

(57) ABSTRACT

This invention relates to novel dicationic and polycationic monoprimary alcohol compounds and their derivatives, represented by the formula

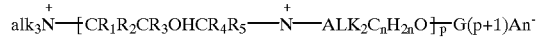

wherein each alk is independently alkyl of 1–8 carbon atoms; each ALK is independently alkyl of 1–8 carbon atoms; each $R_1$, $R_2$, $R_3$, $R_4$ or $R_5$ is independently H or alkyl of 1–8 carbon atoms; n is 2–5; G is H, $CR_1R_2CR_3OHCR_4R_5X$ or

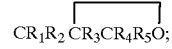

X is Cl, Br or I; $An^-$ is an anion and p is 1–10; provided that the compound is soluble in water.

32 Claims, 1 Drawing Sheet

REACTION SOLUTION IN D₂O

DICATIONIC AND POLYCATIONIC MONOPRIMARY ALCOHOLS AND DERIVATIVES THEREOF

TECHNICAL FIELD

This invention relates to novel dicationic and polycationic monoprimary alcohols and functional derivatives thereof. The novel compounds are characterized by having a single primary hydroxyl function, which permits the dicationic or polycationic alcohols to be used in making derivatives which are not crosslinked, as is a problem presented by dicationic or polycationic diols or polyols, known in the art.

BACKGROUND ART

Representative references disclosing dicationic or polycationic compounds, containing hydroxyl functionality, include Lewis et al. (U.S. Pat. No. 3,567,729), Matter et al. (U.S. Pat. No. 3,632,559), Evani et al. (U.S. Pat. No. 4,156,775), Hoppe et al. (U.S. Pat. No. 4,093,605) and Bachem et al. (U.S. Pat. No. 4,737,576). The compounds disclosed by these references are generally symmetrical in structure and have a plurality of secondary hydroxyl functions. The compounds are often not highly reactive, or selectively reactive, for example, with starch. Use of these compounds, for example, to prepare cationic starch, give products which are more or less highly cross-linked and which may be unacceptable for many utilities.

It is an object of this invention to provide novel dicationic or more-highly cationic monoprimary alcohols, which can be used to prepare highly cationized derivatives, for example, of starch, without presenting a problem of undesired cross-linking of the thus-treated starch.

DISCLOSURE OF INVENTION

This invention relates to compounds of the general formula

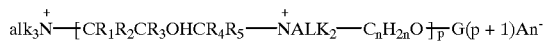

wherein each alk is independently alkyl of 1–8 carbon atoms; each ALK is independently alkyl of 1–8 carbon atoms; each $R_1$, $R_2$, $R_3$, $R_4$ or $R_5$ is independently H or alkyl of 1–8 carbon atoms; n is 2–5; G is H, $CR_1R_2CR_3OHCR_4R_5X$ or

X is Cl, Br or I; $An^-$ is a monovalent anion and p is 1–10, provided that the compound is soluble in water.

In another aspect, this invention relates to cationic starch, obtained by reaction between starch and a compound of the foregoing general formula, wherein G is

or $CR_1R_2CR_3OHCR_4R_5X$.

This invention also relates to a process for making a dicationic monoprimary alcohol, comprising reacting a halohydroxyalkyl trialkylammonium halide of the formula

wherein each alk is independently of 1–8 carbon atoms; each $R_1$, $R_2$, $R_3$, $R_4$ and $R_5$ is independently H or alkyl of 1–8 carbon atoms; X is Cl, Br or I and $X^-$ is $Cl^-$, $Br^-$ or $I^-$ with a dialkylalkanolamine of the formula $ALK_2NC_nH_{2n}OH$, wherein each alkaline material to produce a dicationic alcohol.

This invention further relates to a method of treating paper furnish, comprising adding to the paper furnish a thus-prepared cationic starch.

In another aspect, this invention relates to a method for flocculating solids in waste waters, comprising adding to the waters being treated a compound of the general formula, wherein G is H, in an amount sufficient to flocculate the solids.

DETAILED DESCRIPTION OF THE INVENTION

The compounds of this invention can be prepared by the following general procedure, starting from a chloro-2-hydroxypropyl trialkylammonium chloride:

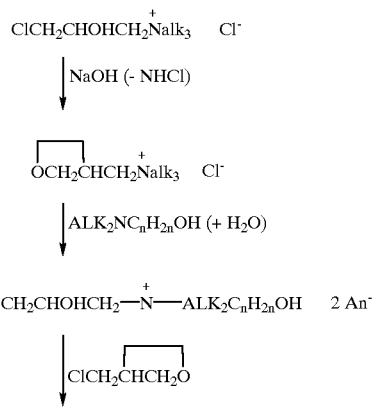

-continued

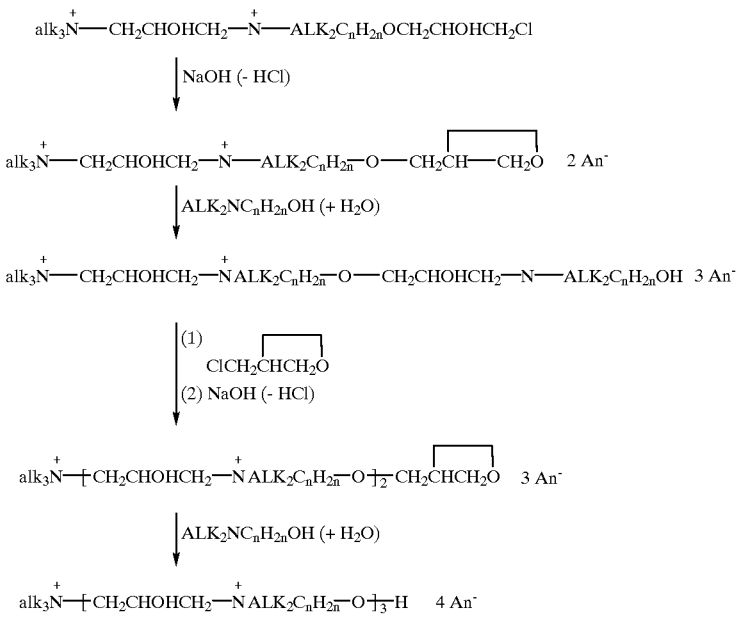

wherein alk is alkyl of 1–8 carbon atoms; ALK is alkyl of 1–8 carbon atoms; and is n is 2–5.

In the first step of the process a 3-chloro-2-hydroxypropyl trialkylammonium chloride, for example, 3-chloro-2-hydroxypropyl trimethylammonium chloride, is converted to an epoxide by dehydrohalogenation with an alkaline material, for example, sodium hydroxide. This starting material corresponds to a compound in which each alk is methyl. 3-Chloro-2-hydroxypropyl trimethylammonium chloride can be prepared and purified as disclosed by Langher et al. (U.S. Pat. No. 3,532,751) and Tasset (U.S. Pat. No. 4,602,110), herein incorporated by reference.

The alkaline material can be selected from alkali metal and alkali earth metal oxides, hydroxides and carbonates. Representative alkaline materials include sodium hydroxide, potassium hydroxide, lithium hydroxide, sodium oxide, sodium carbonate, sodium bicarbonate nahcolite, calcium oxide, calcium hydroxide and calcium carbonate, magnesium oxide, magnesium hydroxide, magnesium carbonate, dolime and the like. Mixtures of alkaline materials can be used. Of the foregoing alkaline materials, sodium and potassium hydroxides are preferred.

The reaction is generally carried out in an aqueous medium with cooling, generally to 0° C. to 50° C. The amount of alkaline material used for converting the halohydrin to the epoxide is at least one equivalent of alkaline material per equivalent of halohydrin. Preferably, a slight excess of alkaline material is used, preferably of the order of 1.05–1.15 equivalent of alkaline material per equivalent of halohydrin. The thus-prepared 2,3-epoxypropyl trialkylammonium is used without further purification for the next step of the synthesis.

It will be understood that preparation of the 2,3-epoxypropyl trialkylammonium chloride need not be carried out immediately before use, should this material be available in large quantities from another source.

The intermediate 2,3-epoxypropyl trialkylammonium halide, in this case, 2,3-epoxypropyl trimethylammonium chloride, is reacted with a dialkylaminoalkanolamine, represented in the schematic formulation as $ALK_2C_nH_{2n}OH$. In a typical case, the dialkylaminoalkanolamine is N,N-dimethylethanolamine, that is, a compound wherein each alk is methyl and n is 2.

Condensation of the 2,3-epoxypropyl trialkylammonium halide and dialkylalkanolamine is initiated by adding the dialkylalkanolamine to a chilled solution of epoxypropyl trialkylammonium chloride in small amounts, preferably by dropwise addition. After all of the dialkylalkanolamine is added and the exothermic reaction has subsided, the reaction mixture is heated to cause the reaction to go to completion. Heating at 40–70° C. is generally preferred, so as to accomplish completion of the reaction within a reasonable time. The progress of the reaction can be followed by high pressure liquid chromatography (HPLC). The disappearance of starting epoxide or maintenance of a constant level of unreacted dialkylalkanolamine can be used as measures of the extent of reaction. In the case of a reaction using dimethylethanolamine, the reaction is usually complete after 5 hours' heating at about 50° C.

Initial isolation of the product is accomplished by adjusting the pH of the resulting mixture to about 2.0, using, for example, hydrochloric acid. It will be understood that the acid selected determines the anion or anions, which are present in the complex and that any strong mineral or organic acid, for example, sulfuric acid, trifluoroacetic acid, chloroacetic acid, can be used for this purpose.

Following removal of residual dialkylalkanolamine from the reaction mixture, conveniently by freeze drying, crude reaction product, which corresponds to a dicationic monoprimary alcohol of this invention, is usually an oily material. The crude dicationic monoprimary alcohol is frequently yellowish in color.

The thus-prepared dicationic monoprimary alcohol can be purified by being taken up in hot isopropanol and filtered to remove salt by-products of the reaction. Solvent can be evaporated from the filtrate using, for example, a rotary evaporator, to produce a hygroscopic white powdery product. It is preferred to store the dicationic monoprimary alcohol under nitrogen or other dry inert gas, should the product not be used immediately after preparation.

The dicationic monoprimary alcohol, of the general formula

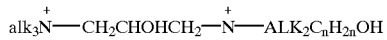

can be converted directly to an epoxide by reaction with epichlorohydrin and an alkaline material. The chlorohydrin can be prepared from the epoxide by addition of hydrochloric acid. The chlorohydrin is generally preferred to the epoxide for storage stability.

It is preferred to carry out the reaction in a solvent, of which the lower alkanols are representative. The lower alkanols include isopropanol, n-butanol, isobutanol, sec-butanol and tert-butanol, as well as the various amyl alcohols. Secondary alcohols, including isopropanol and isobutanol, are preferred solvents. Isopropanol is presently a most preferred solvent for this reaction. The dicationic monoprimary alcohol is dissolved in the solvent by heating above room temperature, preferably at 40–60° C., for a time sufficient to dissolve the dicationic monoprimary alcohol. This is frequently accomplished by heating between 30 min and 3 h. Alkaline material is added to the mixture in an amount at least equivalent to the expected hydrogen halide by-product. It is preferred to use an excess of alkaline material, preferably 1.5 to 3.0 equivalents of alkaline material per mole of hydrogen halide expected from the reaction. If the pH is less than 13, additional alkaline material is added to bring the pH to 13. Epichlorohydrin (about 1 equivalent) is added dropwise to the resulting solution, maintained at 40–60° C., for a time sufficient to complete the reaction. This time varies according to the temperature of the reaction mixture, although the reaction is generally complete within 24 h at 40–60° C.

The progress of the reaction can be followed by HPLC, using disappearance of either dicationic monoprimary alcohol (DCOH) or epichlorohydrin as an indication of the extent of reaction. In a typical case, the final reaction mixture contains more than 85% by weight of dicationic epoxide, plus monocationic and dicationic alcohols.

The resulting dicationic epoxide (G is

can be used for any reaction, in which an epoxide ring is required. A preferred utility for dicationic monoepoxides of this invention is for the preparation of highly cationized starch, which does not tend to be crosslinked. Cationic starches, prepared using the dicationic monoepoxides of this invention, can be used as additives for making papers, particularly as flocculating agents in the paper furnish to facilitate settling of pigments and paper fibers in the web being formed on the paper making machinery.

In addition, the dicationic monoepoxide thus prepared can be treated with a dialkylaminoalkanolamine to produce a tricationic monoprimary alcohol. The procedure followed will be the same as disclosed for making a dicationic primary alcohol from an epoxypropyl trialkylammonium chloride and a dialkylalkanolamine.

The thus-produced tricationic monoprimary alcohol can be converted to an epoxide by treatment with epichlorhydrin and an alkaline material, generally under conditions disclosed above for reaction between epichlorhydrin and dicationic primary alcohol.

The preparation of polycationic monoprimary alkanols can be carried out by stepwise reaction between an intermediate cationic primary alcohol and epichlorohydrin, followed by reaction with a dialkylaminoalkanolamine.

It will be understood that the reaction sequence can be initiated using 3-iodo or 3-bromo-2-hydroxylpropyl trialkylammonium bromides/iodides as well as the chlorohydroxypropyl trialkylammonium chlorides. When starting materials are being selected, alkyl (alk) can be selected from alkyl of 1–8 carbon atoms, including the various isomers. Owing to the need for water solubility, preferred species of alk are methyl and ethyl.

When compounds, wherein any of $R_1$, $R_2$, $R_3$, $R_4$ or $R_5$ is other than H, are to be prepared, the starting material will be a higher epoxyhaloalkane, represented by the formula

Representative higher epoxyhaloalkanes include butylene chlorohydrin, 2,3-epoxy-1-chloropentane ($R_1$=$C_2H_5$, $R_2$=H), 2,3-epoxy-1-bromohexane ($R_1$=$C_3H_7$, $R_2$=H), and the like. These epoxides can be made by oxidation of unsaturated halides. They can be converted to halohydroxyalkyl quaternary ammonium salts by reaction with a tertiary amine, alk$_3$N. The use of 3-chloro-2-hydroxypropyl trialkylammonium halides, derived from epihalohydrins, is preferred.

The dialkylalkanolamines, represented by the general formula $ALK_2NC_n$—$H_{2n}OH$, are compounds wherein each ALK is independently selected from alkyl of 1–8 carbon atoms, including various isomeric alkyl groups. Preferred alkyl groups are methyl and ethyl. The value of n can be varied from 2 to 5 and includes various isomeric carbon skeletons. Preferred dialkylalkanolamines are dialkylethanolamine, dialkylisopropanolamine, dialkylpropanolamine, dialkylbutanolamine and dialkylisobutanolamine. Most preferred are dialkylethanolamine, dialkylisopropanolamine and dialkylpropanolamine, wherein n is 2 or 3. Most preferred dialkylalkanolamines are therefore dimethyl- or diethylethanolamine, isopropanolamine or propanolamine, wherein alk is methyl or ethyl and n is 2 or 3.

The anion component will depend upon the pH of the mixture and on the anion of the acid/acids used for neutralization. It will be understood that $An^-$ includes monovalent and equivalent anions, for example, chloride, bromide, iodide, trichloroacetate, bisulfate, ½ $SO_4^=$, ⅓ $PO_4^{-3}$, ½ $HPO_4^=$, and the like.

At the end of the reaction with the dialkylalkanolamine, the product corresponds to a compound of the general formula, wherein G is H. This product can be chain-extended by reaction in sequence with epoxyhaloalkane, to give an intermediate having a terminal fragment (G) of the structure $CR_1R_2CR_3OH$—$CR_4R_5X$, which can be chain-extended by reaction with a dialkylalkanolamine, under conditions similar to those disclosed above. When the terminal fragment (G) is derived from an epihalohydrin, it is represented by the structure $CH_2CHOH$—$CH_2X$ and can be cyclized to an epoxide function by treatment with an alkaline material, as above.

The dicationic monoprimary alcohols of this invention (G is H) can be used in the paper industry, for example, to improve pigment retention. The products are added to the paper furnish at the headbox and the paper furnish is processed by conventional techniques. See, for example, Hoppe et al., U.S. Pat. No. 4,093,605, above.

The cationic starches of this invention are particularly useful for improving pigment retention in papers, containing significant amounts of recycled fibers. The recycled fibers are shorter and smoother than virgin fibers. Repeatedly recycled fibers gradually lose strength and bonding abilities, as a result of which papers containing large amounts of recycled short pulp fibers retain pigments less readily than papers, made from virgin fibers.

The amount of dicationic or polycationic starch to be put in the paper furnish can be determined by routine experimentation, using evaluation methods known to those skilled in the art. See, generally, Wurzburg, ed., "Modified Starches: Properties and Uses," CRC Press, Inc., Boca Raton Fla., (1986), page 122.

The dicationic and polycationic monoprimary alcohols can be used in water purification processes, particularly as a flocculating agent. The products are applied by techniques of which those of Buckman et al. (U.S. Pat. No. 4,054,542) and Witt (U.S. Pat. No. 3,755,160), herein incorporated by reference, are typical. The dosage of active compound is approximated by laboratory settling tests and adjusted during use in the field.

A particularly preferred use for the products of this invention is for the preparation of cationic starch. In addition to avoiding crosslinking of the starch, the products of this invention give products with significantly higher cationicity than obtainable heretofore. The products used for preparation of cationic starch are those wherein G is $CR_1R_2CR_3OHCR_4R_5X$ or

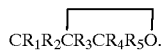

Techniques for preparing cationic starches are disclosed by Jarowenko et al. (U.S. Pat. No. 4,281,109), Rankin et al. (U.S. Pat. No. 4,127,563), Fischer et al. (U.S. Pat. No. 4,332,935) and Tasset (U.S. Pat. No. 4,464,528), herein incorporated by reference. These references also teach methods of using cationic starch products.

Starches include amylaceous substances, whether modified or unmodified, which contain free hydroxyl groups. Starches include modified, as well as acid modified, dextrinized, hydrolyzed, oxidized and derivatived starches, including starch ethers and starch esters which retain reactive hydroxyl sites. The starches can be obtained from a variety of sources, including but not limited to, corn, wheat, potato, tapioca, waxy maize, sago, rice or barley, as well as high amylose starches, including amylose or amylopectin starch fractions.

BEST MODE FOR CARRYING OUT THE INVENTION

Figure 1:
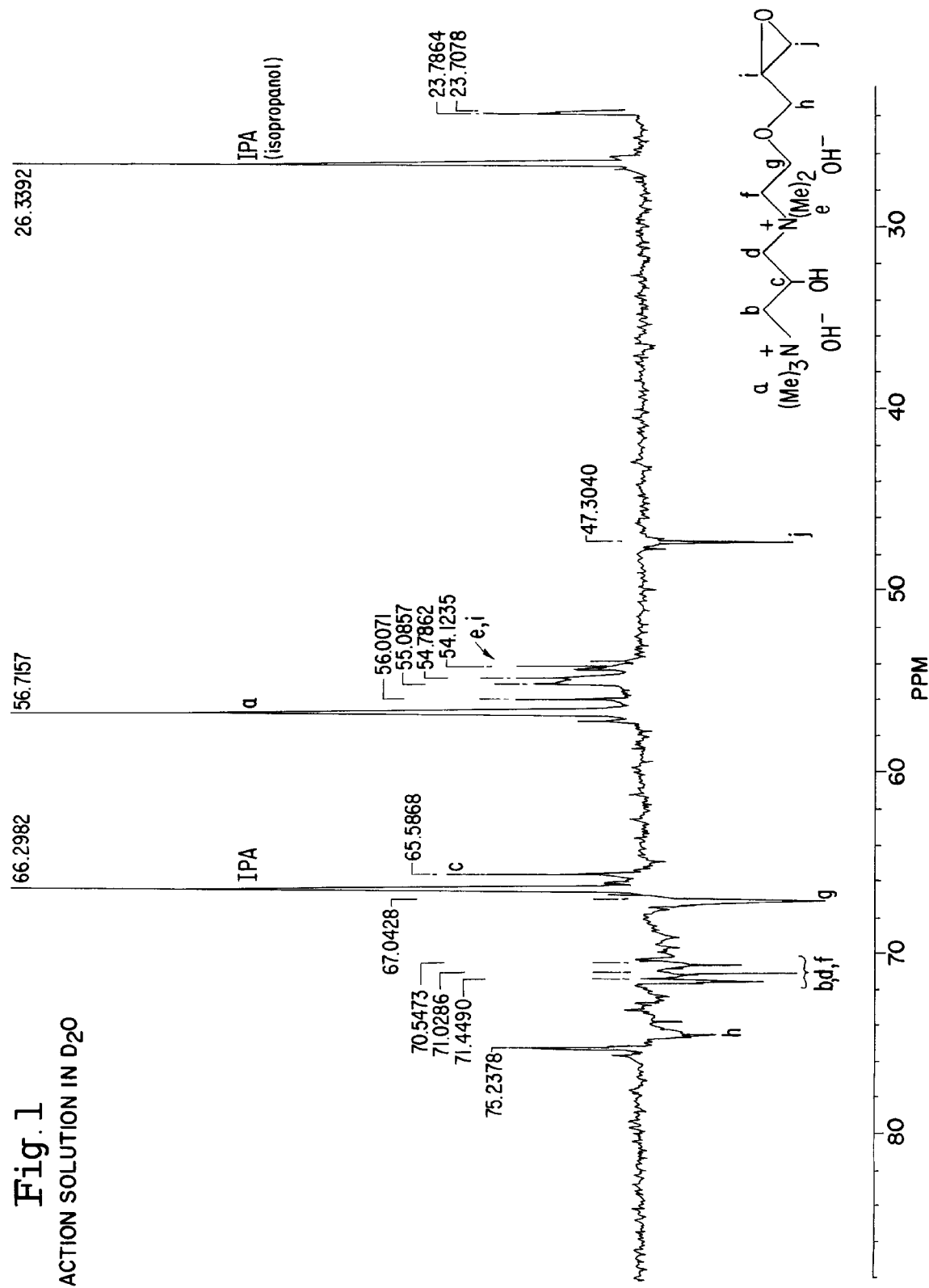
In FIG. 1 is shown the NMR spectrum of a dicationic epoxide, prepared in accordance with this invention.

Most preferred compounds of this invention are those wherein each of $R_1$, $R_2$, $R_3$ $R_4$ and $R_5$ is H; each alk is methyl or ethyl; each ALK is methyl or ethyl; n is 2 or 3; p is 1 or 2 and $An^-$ is $OH^-$ or $Cl^-$ or a mixture thereof. Most preferably, G is H, $CH_2CHOHCH_2Cl$ or

Most preferably, starch is cationized with a compound, as above, wherein G is

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

(a) Reaction Between 3-Chloro-2-hydroxypropyltrimethyl Ammonium Chloride and Dimethylethanolamine To a 500-mL round bottom flask is charged 100 g of 3-chloro-2-hydroxypropyltrimethyl ammonium chloride (CHPTMAC, 0.53 mol) and 100 mL of water. The mixture is stirred and chilled to 0° C. using an ice-salt bath. To the resulting mixture is added 1.1 equivalent of 25% NaOH solution (by weight) at a rate such that the temperature does not go above 5° C. The resulting mixture is allowed to stir at 0–5° C. for 10 min. Dimethylethanolamine (DMEA, 1.0 equivalent) is added to the chilled epoxidized solution.

The contents of the flask are allowed to warm to room temperature and then slowly heated to 50° C. The temperature is held at 50° C. for 5 h or until HPLC analysis indicates that the reactants have been consumed. The pH of the solution is measured and 50% HCl is added to bring pH to about 2.0.

The resulting solution of crude dicationic alcohol (DCOH) is placed in a freeze dryer and water is removed. Any unreacted DMEA will be removed during this step. The purity of the resulting product is 89.99%.

The resulting oily solid is dissolved in hot isopropanol with stirring. The hot solution is filtered to remove any salts. The filtrate is cooled before evaporating the isopropanol to obtain purified DCOH crystals. The solid product is stored under nitrogen.

(b) Conversion of Dicationic Alcohol to Dicationic Epoxide

Dicationic alcohol (DCOH, prepared in part (a), 4.1832 g, 0.0150 mol) is dissolved, with stirring and heating at 45° C., in 10 g of isopropanol The solution is heated at 45° C. for at least one h. To the warm solution is added 1.2 g (2 equivalents) of crushed sodium hydroxide. The resulting mixture is stirred at 45° C. for 1 h. The warm solution is filtered to remove salt, after which the filtrate is returned to the reaction flask. The pH of the solution is measured. Additional sodium hydroxide is added, if required, to bring pH to 13.0.

To the resulting solution, 1.0 equivalent of epichlorohydrin is added dropwise. The resulting mixture is allowed to react for 22 h, during which the temperature of the reaction mixture is maintained at 45° C. The pH at this point is about 12. HPLC analysis demonstrates disappearance of both the DCOH and the epichlorohydrin. The solution contains 85.2% of dicationic epoxide (DCE). The remainder is monocationic and dicationic glycols.

The NMR sprectum of DCE, prepared as above, from CMPTMAC, DMEA and epichlorohydrin is shown in FIG. 1.

(c) Conversion of Dicationic Alcohol to Dicationic Epoxide

A reaction is run as in (b) and followed by HPLC analysis. It is found that most of the reaction to produce dicationic epoxide occurs within the first hour and that the reaction is essentially complete within 5 h.

(d) Work-Up of DCOH Using tert-Butanol

A reaction mixture, obtained as in (a), is purified using tert-butanol, rather than isopropanol. Similar results are obtained.

(e) Identification of Reaction By-Products

A by-product of the reaction of (b) is identified by HPLC and NMR as a reaction product from isopropanol and epichlorohydrin. This material contains no nitrogen. It is thought that this by-product does not interfere with use of the products.

EXAMPLE 2

Cationization of Starch With DCE

DCE, prepared as in Example 1(b) is used to produce cationic starch according to the procedure of Carr et al., "Preparation of Cationic Starch Ether: A Reaction Efficiency Study," Die Starke. vol. 33 (1981), page 310. The starch was lightly cationized (Kjeldahl analysis).

To a 500-mL round-bottom flask is charged 133.1 g of distilled water, which is heated to 50° C. To the warm water is added 50.1 g of sodium sulfate and 80.81 g of pearl starch. The material in the flask is mixed to produce a homogeneous mixture, to which is added solid crushed sodium hydroxide (1.7529 g), followed by 15.7708 g of crude, freshly-made DCOH. The DCOH activity is about 0.224 mol (HPLC).

The resulting solution is allowed to react at 50° C. for 4 h, at which point the solution is poured into a 4-L beaker, containing a pH electrode. Hydrochloric acid (6N) is added to the contents of the beaker until pH is below 6. The resulting solution is stirred for 10 mn and then filtered with vacuum. The filtercake is returned to the beaker and slurried with 2 L of distilled water over 10 min. Filtration and washing is repeated twice more. The cationic starch is then washed with 95% ethanol. The cationized starch is dried overnight in a vacuum oven. Kjeldahl analysis indicates that the starch is lightly cationized.

Use of cationic starch in paper making reduces biological oxygen demand (BOD) of the white water, improves retention of fines and filler, increases strength and increases the drainage rate of the pulp.

EXAMPLE 3

Conversion of Dicationic Epoxide to Chlorohydrin

A solution of dicationic epoxide of Example 1(b) is converted to a stable chlorohydrin by treatment with 25% HCl to pH 3.

EXAMPLE 4

Preparation of Polycationic Monoprimary Alcohol

The epoxide of Example 1(b) is reacted with dimethylethanolamine, as in Example 1(a), to produce a tricationic alcohol This is reacted with epichlorohydrin, in the presence of sodium hydroxide, to produce a tricationic epoxide.

The product is treated stepwise with dimethylethanolamine and epichlorohydrin/sodium hydroxide to produce monoprimary alcohols of any degree of cationicity.

EXAMPLE 5

3-Chloro-2-hydroxypropyl trimethylammonium chloride is converted to 2,3-epoxypropyl trimethylammonium chloride by reaction with sodium carbonate, using conditions otherwise as in Example 1(a). The epoxide is reacted with diethylisopropanolamine, then with 2,3-epoxy-1-chlorobutane/sodium hydroxide, and then with diethylisopropanolamine.

The product is useful for flocculating solids in waste waters.

EXAMPLE 6

Use of Cationic Starch in Papermaking (a) Conventional Paper Furnish

The cationic starch of Example 2 is added to paper making furnish, made from virgin cellulosic pulp. Good drainage rates and pigment retention are observed.

(b) Paper Furnish Containing Recycled Fibers

Paper making furnish, containing recycled preconsumer and postconsumer fibers, is prepared. Use of cationic starch, as prepared in Example 2, improves the pigment and filler retention properties of the resulting paper.

The preceding examples can be repeated with similar success by substituting the generically or specifically described reactants and/or operating conditons of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula

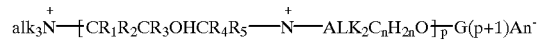

wherein each alk is independently alkyl of 1–8 carbon atoms; each of $R_1$, $R_2$, $R_3$, $R_4$ and $R_5$ is independently H or alkyl of 1–8 carbon atoms; each ALK is independently alkyl of 1–8 carbon atoms; n is 2–5; G is H, $CR_1R_2CR_3OHCR_4R_5X$ or

X is Cl, Br or I; p is 1–10 and An⁻ is an anion; provided that the compound is soluble in water.

2. A compound of claim 1, wherein each of $R_1$, $R_2$, $R_3$, $R_4$ and $R_5$ is H.

3. A compound of claim 1, wherein each alk is methyl or ethyl.

4. A compound of claim 1, wherein each ALK is methyl or ethyl.

5. A compound of claim 1, wherein n is 2 or 3.

6. A compound of claim 1, wherein p is 1 or 2.

7. A compound of claim 1, wherein An⁻ is Cl⁻ or OH⁻ or a mixture thereof.

8. A compound of claim 1, where each of $R_1$, $R_2$, $R_3$, $R_4$ and $R_5$ is H; each alk is methyl or ethyl; each ALK is methyl or ethyl; n is 2 or 3; p is 1 or 2 and $An^-$ is $Cl^-$ or $OH^-$ or a mixture thereof.

9. A compound of claim 1, wherein G is H.

10. A compound of claim 1, wherein G is $CR_1R_2CR_3OHCR_4R_5X$.

11. A compound of claim 1, wherein G is $CH_2CHOHCH_2Cl$.

12. A compound of claim 1, wherein G is

13. A compound of claim 1, wherein G is

14. A compound of claim 1, wherein each of $R_1$, $R_2$, $R_3$, $R_4$ and $R_5$ is H; each alk is methyl or ethyl; each ALK is methyl or ethyl; n is 2 or 3; p is 1 or 2; G is $CR_1R_2CR_3OHCR_4R_5Cl$; and $An^-$ is $Cl^-$ or $OH^-$ or a mixture thereof.

15. A compound of claim 1, wherein each of $R_1$, $R_2$, $R_3$, $R_4$ and $R_5$ is H; each alk is methyl or ethyl; each ALK is methyl or ethyl; n is 2 or 3; p is 1 or 2; G is $CH_2CHOHCH_2Cl$; and $An^-$ is $Cl^-$ or $OH^-$ or a mixture thereof.

16. A compound of claim 1, wherein each of $R_1$, $R_2$, $R_3$, $R_4$ and $R_5$ is H; each alk is methyl or ethyl; each ALK is methyl or ethyl; n is 2 or 3; p is 1 or 2; G is H; and $An^-$ is $Cl^-$ or $OH^-$ or a mixture thereof.

17. A compound of claim 1, wherein each of $R_1$, $R_2$, $R_3$, $R_4$ and $R_5$ is H; each alk is methyl or ethyl; each ALK is methyl or ethyl; n is 2 or 3; p is 1 or 2; G is

and $An^-$ is $Cl^-$ or $OH^-$ or a mixture thereof.

18. A compound of claim 9, wherein each of $R_1$, $R_2$, $R_3$, $R_4$ and $R_5$ is H.

19. A compound of claim 9, wherein each alk is methyl or ethyl.

20. A compound of claim 9, wherein each ALK is methyl or ethyl.

21. A compound of claim 9, wherein n is 2 or 3.

22. A compound of claim 9, wherein p is 1 or 2.

23. A compound of claim 10, wherein each of $R_1$, $R_2$, $R_3$, $R_4$ and $R_5$ is H.

24. A compound of claim 10, wherein each alk is methyl or ethyl.

25. A compound of claim 10, wherein each ALK is methyl or ethyl.

26. A compound of claim 10, wherein n is 2 or 3.

27. A compound of claim 10, wherein p is 1 or 2.

28. A compound of claim 12, wherein each of $R_1$, $R_2$, $R_3$, $R_4$ and $R_5$ is H.

29. A compound of claim 12, wherein each alk is methyl or ethyl.

30. A compound of claim 12, wherein each ALK is methyl or ethyl.

31. A compound of claim 12, wherein n is 2 or 3.

32. A compound of claim 12, wherein p is 1 or 2.

* * * * *